United States Patent [19]

Edwards et al.

[11] Patent Number: 5,025,829
[45] Date of Patent: Jun. 25, 1991

[54] PARENTERAL CHECK VALVE

[75] Inventors: Floyd V. Edwards, Eggertsville; Scott H. DeWitt, Lockport, both of N.Y.

[73] Assignee: Harmac Medical Products, Inc., Buffalo, N.Y.

[21] Appl. No.: 471,876

[22] Filed: Jan. 29, 1990

[51] Int. Cl.⁵ ........................................... F16K 15/14
[52] U.S. Cl. .................................. 137/512; 137/859; 251/368; 604/247
[58] Field of Search ............... 604/247; 137/512, 859; 251/368

[56] References Cited

U.S. PATENT DOCUMENTS

| | | | |
|---|---|---|---|
| 2,497,906 | 2/1950 | Peters | 137/859 X |
| 2,758,609 | 8/1956 | Dickert | 137/859 |
| 3,176,712 | 4/1965 | Ramsden | 137/859 X |
| 3,827,456 | 8/1974 | Sheppard | 137/859 |
| 4,593,720 | 6/1986 | Bergandy | 137/859 |
| 4,712,583 | 7/1987 | Pelmulder | 137/859 X |

FOREIGN PATENT DOCUMENTS 751289  6/1956  United Kingdom ................ 137/859

Primary Examiner—Robert G. Nilson

Attorney, Agent, or Firm—Woodcock Washburn Kurtz Mackiewicz & Norris

[57] ABSTRACT

A check valve, including an inlet housing portion and outlet housing portion which are adapted to be snap-fit together, is inexpensively and quickly produced using valve disks which are capable of providing variable fluid flow resistance. The valve disk is stamped from flexible materials having a Shore A durometer hardness in the range of from about thirty to about one hundred (e.g., a thermoplastic elastomer). Flat, circular shapes having at least three, arcuately-shaped windows defined therein, with an outer sealing periphery being joined to a circular closing member by webs which separate the windows, provide a valve disk of substantial manufacture ease. The check valve is adapted to be used in primary and secondary solution lines, and its variable resistance to fluid flow is enable by merely increasing or decreasing the combined surface area of the windows, increasing or decreasing a preload provided by extending a valve seat in the inlet housing towards the valve disk, increasing or decreasing thicknesses of a valve disk, or varying the proportion of the diameters of the closing member to the valve seat.

17 Claims, 2 Drawing Sheets

PARENTERAL CHECK VALVE

BACKGROUND OF THE INVENTION

1. Field of the Invention

This invention relates generally to apparatus used to regulate fluid flow in medical devices, and more particularly to check valves for such apparatus.

2. Statement of the Prior Art

For ease of manufacture, there have been proposed many styles of check valves in the prior art. See, for example, U.S. Pat. Nos. 2,462,189 (Hess); 2,497,906 (Peters et al.); 4,141,379 (Manske); and 4,712,583 (Pelmulder et al.); and, a Japanese Application No. 58-77980 (Okumura). Unfortunately, the check valves that are most easily manufactured frequently suffer from weepage and leakage problems, as well as an inability to be variably set for different "cracking pressures". These cracking pressures, as is well known, constitute the pressures at which a check valve will open but below which it will stay closed.

In the administration of medical solutions, check valves are very important. A typical case is where primary lines of such solutions (e.g., saline or dextrose solutions) are administered from intravenous bags through flexible tubing to a patient having an intravenous (IV) needle. Solution is delivered to the patient by any conventional delivery means such as gravity flow, pressure cuffs, syringe pumps or peristaltic pumps. Valves such as disclosed in the aforementioned U.S. Pat. No. 4,712,583 (Pelmulder et al.) are necessary with such systems to provide for careful control in the administration of the solution.

Secondary lines may also be used in the administration of different solutions. For example, saline solution may be administered through the primary line of a system, and at the same time a secondary medication may be administered through a secondary line that is connected by way of a Y-fitting. These systems which employ both a primary and a secondary line may require check valves in both lines, but the particular requirements for each check valve may be different. In valves used for a primary line, for example, an "antireflux" type valve is necessary. The conventional antireflux valve must open very rapidly, yet have a minimum hysteresis in the reverse direction. Accordingly, these antireflux valves are usually complex in their design as well as their manufacture. The Pelmulder et al. patent is indicative of such complex designs.

Check valves which are used in the secondary lines for administration of secondary solutions have different requirements from their antireflux valve counterparts. That is, in this type of "piggyback" medication therapy, the check valves should be preloaded to provide increased cracking pressure while at the same time protecting against the case of occlusion alarms where blockages cause tremendous backflows in the secondary line. Furthermore, check valves used in secondary lines must be capable of preventing a flow of the secondary medication unless and until flow is established in the primary line.

A problem with previous check valves used with apparatus to administer medical solutions is their complexity of design and manufacture. Such complexity can increase their costs, and prevent their adaptation to variable settings. For example, the cracking pressure required of a particular check valve is dependent on the application in which the valve is used. In view of a multitude of applications, a check valve design capable of a multitude of cracking pressures is necessary. Consequently, a need exists for a check valve which is inexpensive and of a design adaptable to variable settings.

SUMMARY OF THE INVENTION

Accordingly, it is a general object of this invention to provide a valve disk for check valves that is simple in its design and manufacture. It is a more particular object of the present invention to provide a check valve that is easy to produce and quickly adapted for differing applications.

It is another object of the invention to provide a check valve for administration of solutions in both a primary and a secondary line of piggyback medication therapy.

It is still another object of this invention to provide a system for administration of solutions which employs check valves of the type disclosed herein.

Briefly, these and other objects according to the present invention are accomplished by a valve disk which comprises a flat, circular piece of flexible material. The piece is quickly produced such as by stamping or molding to form an outer sealing ring at its periphery, at least three arcuately-shaped windows substantially evenly-spaced radially inward from the outer sealing ring, and a circular closing member concentrically disposed radially inward from the windows and joined to the outer sealing ring by a plurality of webs.

In accordance with one important aspect of the invention, such valve disk is installed between a first housing portion having an inlet and a valve seat, and a second housing portion having an outlet. Both housing portions have a valve disk retaining surface with an annular ridge protruding therefrom. In such a manner, the valve disk is retained between the housing portions by the annular ridges contacting its outer sealing ring. The valve seat which is formed in the first housing portion may protrude toward the second housing portion by a preselected distance beneath the valve disk retaining surface in the first housing portion. In such a manner, various amounts of preloading are capable with valve disks of the same manufacture.

The particular material that is used for the valve disk suitably comprises a material having a Shore A durometer hardness in the range of about 35 to about 100. Preferably, such material comprises a Shore A durometer hardness of about 55. The material may comprise a thermoplastic material, an elastomeric material or a thermoplastic elastomer. Preferably, a thermoplastic elastomer is used for the valve disk. Other factors, such as the thickness of the valve disk, a combined area of the windows formed therein, as well as the number of windows, and a ratio of the diameter of the closing member to the diameter of the inlet will also affect the cracking pressure of check valves according to the invention. However, because the valve disk is formed as a flat, circular piece of flexible material that does not require complex manufacturing operations, such variables can be taken into account to provide an adaptable check valve. The housing portions are, also, preferably formed to be snap-fit together, thereby leading to more advantageous manufacture of the check valve.

According to another important aspect of the invention, the check valve is used in a system for administering solutions having primary and secondary lines. Since check valves as described herein are so adaptable and variably set, they may be used as antireflux valves in the primary lines of such systems, or as a typical check valve in the secondary lines.

Other objects, advantages and novel features according to this invention will become more apparent from the following detailed description thereof, when considered in conjunction with the accompanying drawings wherein:

DETAILED DESCRIPTION OF THE INVENTION

Figure 1:
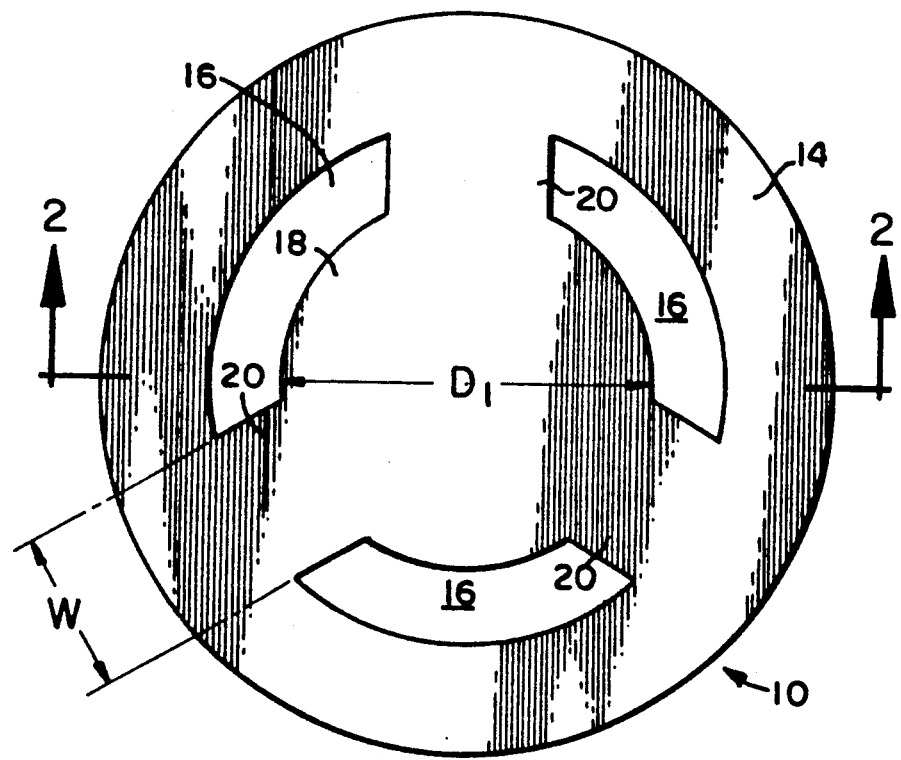
FIG. 1 is a plan view of a valve disk according to the present invention.

Referring now to the drawings, wherein similar element numbers designate like or corresponding parts throughout each of the several views, there is shown in FIG. 1 a valve disk 10 used in a check valve 12 (FIG. 3) according to the present invention.

The valve disk 10 is formed of a flexible material as a flat, circular shape. Such shape may be formed by stamping and cutting disk 10 in any conventional way or by molding disk 10. The flexible material used for valve disk 10 comprises an elastomeric material, a thermoplastic material or a thermoplastic elastomer. Preferably, such flexible material comprises a material having a Shore A durometer hardness in the range of about 35-100. Exemplary materials which may be used for valve disk 10 are selected from the group consisting of silicone rubber, terpolymers of ethylene, propylene and a diene side chain, which products have been sold under the trademarks "EPT", "EPSYN", "ROYALENE", "VISTALON" and "NORDEL" or thermoplastic elastomers sold under the trademarks "HYTRON", "KRATON" and "SANTOPRENE". A valve disk 10 formed from "KRATON" elastomer is employed in the presently preferred embodiment of this invention.

Figure 2:
FIG. 2 is a sectional view of the valve disk in FIG. 1, taken along the lines 2—2.

As seen in FIGS. 1 and 2, valve disk 10 includes outer sealing ring 14, three arcuately-shaped windows 16 substantially evenly-spaced radially inward from the outer sealing ring 14, and a circular closing member 18 concentrically formed inwardly from the windows 16 joined to the outer sealing ring 14 by three webs 20. In accordance with an important aspect of the invention, at least three such windows 16 must be used with the valve disk 10, but more than three windows 16 may be used for the valve disk 10 to provide a greater amount of surface area for flow. Those of ordinary skill in the art can appreciate that particular amounts of surface area will required for particular applications. As a result, valve disks 10 having three or more windows 16 of various sizes will fall within the scope of the present invention.

Figure 3:
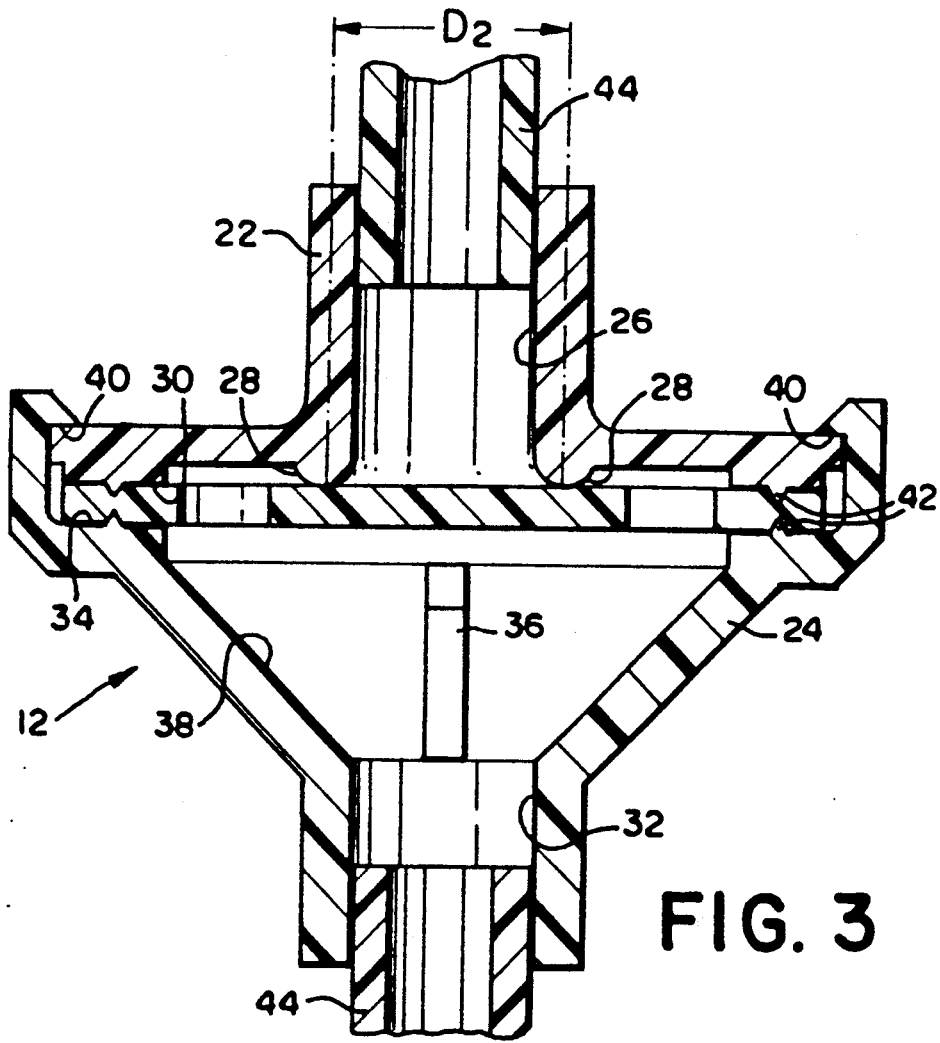
FIG. 3 is a sectional view of a check valve incorporating the valve disk according to the present invention.

Referring now to FIG. 3, in conjunction with FIGS. 1-2, a preferred structure of the check valve 14 will now be explained. Check valve 14 generally comprises a first housing member 22, and a second housing member 24 which are connected together to retain valve disk 10 therebetween. First housing member 22 comprises an inlet 26, a valve seat 28 and one valve disk retaining surface 30 of annular shape. Second housing member 24 includes an outlet 32, another valve disk retaining surface 3 of annular shape and three valve disk support ribs 36 which protrude from an inner wall 38 of the second housing member 24. Preferably, the first 22 and second 24 housing members are both formed of easily manufactured plastic, such as styrene or an acrylic copolymer, although another suitable material may be substituted. Plastics are desirable for the quick and easy way in which they may be formed. As shown in FIG. 3, the first 22 and second 24 housing members are joined together by snap-fit means including a flexible shoulder portion 40 in first housing member 22. It is also within the scope of the present invention to join first 22 and second 24 housing members by other means, such as welding, adhesive, ultrasonic molding or other suitable means.

Figure 4:
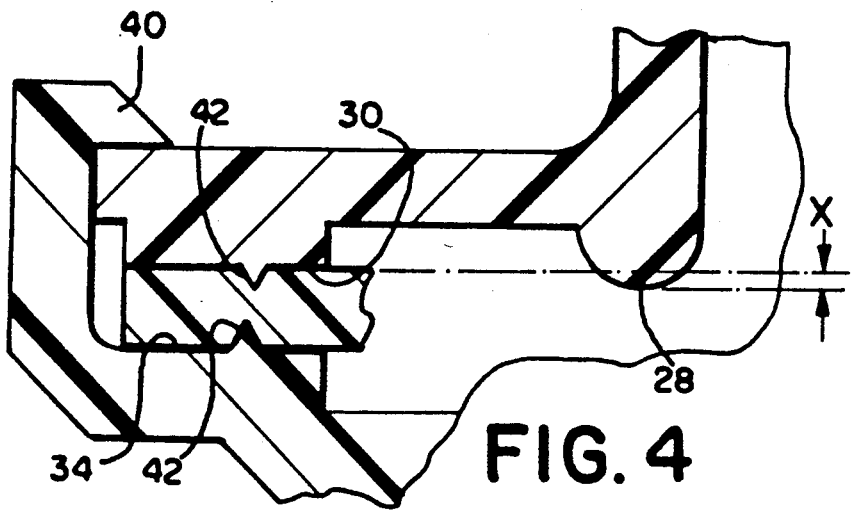
FIG. 4 is an enlarged sectional view of a portion of the check valve in FIG. 3, illustrating means for varying an amount of preloading for the valve disk according to this invention.

As can also be seen in FIG. 3, and in greater detail in FIG. 4, both valve disk retaining surfaces 30, 34 include opposed ridges 42. Each ridge 42 comprises an annular shape, preferably triangular in cross-section, which grasps the outer sealing ring 14 to retain the valve disk 10 tightly within first 22 and second 24 housing members when snap-fit together. However, simple means such as the opposed ridges 42 must be used to provide a seal for check valve 14. The support ribs 36 (only one of which is shown for simplicity) enable deflection of the valve disk 10 to open the check 14 for delivery of solutions from flexible tubing 44 (FIG. 3) at inlet 26 to flexible tubing 44 at outlet 32, while at the same time preventing too much deflection and thereby control flow of the solution.

Referring more specifically now to FIG. 4, it can be seen that valve seat 28 extends beneath valve disk retaining surface 30 of the first housing member 22 by a distance X. The distance X is predetermined to provide a preselected amount of preload for valve disk 10. That is, the greater the distance X for a given structure of valve disk 10, the greater the amount of preload. In turn, the amount of preload provided by the particular predetermined distance X, together with the thickness of the valve disk 10, its particular Shore A durometer hardness, a combined surface area of windows 16, and the number and width W of the webs 20, will provide selectable cracking pressures for check valve 12. Preferably, such cracking pressures comprise from about 0 to about 1.5 psi. One of ordinary skill in this art should be readily capable of producing the valve disk 10 according to this invention, having a variable preselected cracking pressure, without undue experimentation.

Figure 5:
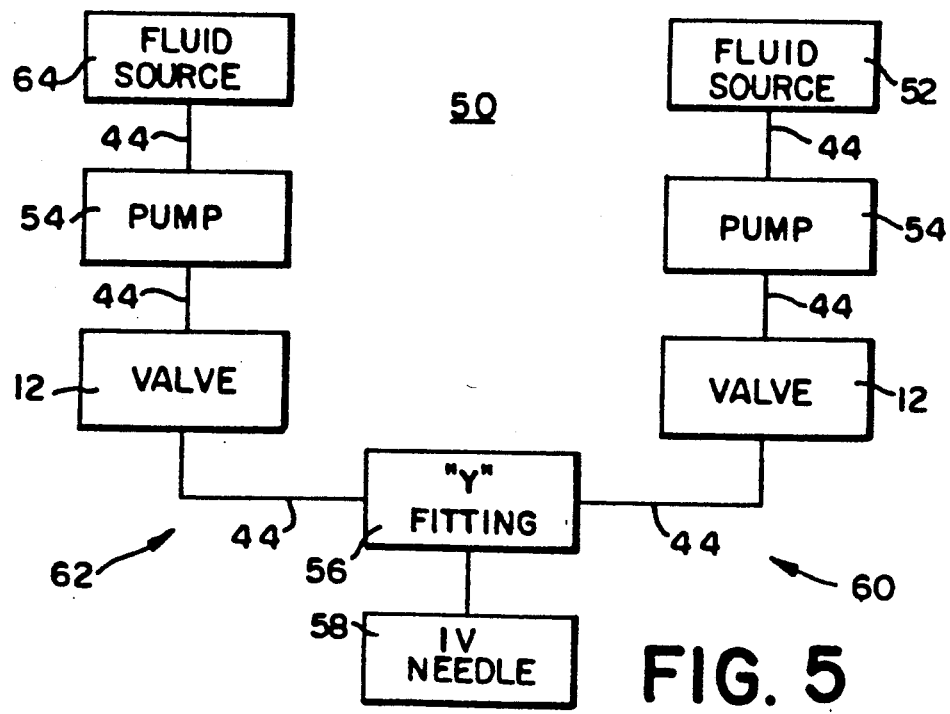
FIG. 5 is a block diagram of a system for administering solutions in accordance with the present invention.

Referring now to FIG. 5, there is shown a system 50 that employs one or more check valves 12 according to the invention for administering solutions in a "piggyback" manner. Fluid source 52 comprises a primary solution such as a saline solution or a dextrose solution which is administered via flexible tubing 44, pump means 54, valve 12, a "Y" fitting 56 and IV needle 58 to a patient (not shown). Pump means 54 suitably comprises any conventional means for delivering the solution, such as by gravity flow, a pressure cuff, a syringe pump, or a peristaltic pump. Valve 12 in the primary line 60 protects the patient from overpressurization by pump means 54. In such an arrangement, valve 12 is referred to as an antireflux valve. Therefore, valve 12 in primary line 60 according to this invention is, preferably, adapted for rapid opening and minimum hysteresis in the direction of the fluid source 52.

A secondary line 62 also comprises a fluid source 64 of secondary medication, pump means 54, valve 12 and flexible tubing 44. Where gravity flow is used to deliver the primary solution contained within fluid source 52, fluid source 64 can be suspended at a level beneath a level of suspended fluid source 52. Similarly, pump means 54 used with the secondary line 62 comprises gravity flow, pressure cuff, syringe pump, peristaltic pump or any other conventional means for delivery of the solutions. Valve 12 in secondary line 62 is preferably preloaded to an amount of about 1.5 psi.

Obviously, many modifications and variations for a valve disk and check valve are possible in light of the above teachings. It is to be understood, therefore, that within a scope of the appended claims the present invention is capable of practice otherwise than is specifically described herein.

What we claim as our invention is:

1. A check valve for use with apparatus to administer solutions, comprising:
   a valve disk, wherein said valve disk comprises:
      a flat, circular piece of flexible material with a Shore A durometer hardness in the range of about 35-100 having at least three arcuately-shaped windows formed in said piece, each adjacent window being separated by a web of predetermined width;
      a sealing annulus at the outer periphery of said piece, said sealing annulus being defined by the formation of said windows; and
      a central closure for closing a valve seat of the check valve, said closure being defined by the formation of said windows concentrically inward from said windows and attached to said sealing annulus by said webs;
   a first housing portion with an inlet adapted to receive a supply conduit, said first housing portion comprising first retaining means for retaining said valve disk;
   a second housing portion with an outlet adapted to receive a discharge conduit, said second housing portion comprising second retaining means for retaining said valve disk, wherein said first and second retaining means each comprise an annular ridge in opposed surfaces of said first and second housing portions;
   wherein said first and second retaining means together with said valve disk sealing said check valve when said first and second housing portions are coupled together; and
   preloading means for preloading said valve disk, wherein said valve disk is adapted to open and close said inlet and wherein said preloading means comprises the valve seat being formed in said first housing portion to protrude therefrom a preselected distance from said surface of said first housing portion.

2. The check valve according to claim 1, wherein said first and second housing are adapted to be snap-fit together.

3. The check valve according to claim 1, wherein each annular ridge comprises a triangular cross-section extending above its respective surface.

4. The check valve according to claim 1, wherein said sealing annulus is adapted to be retained by said first and second retaining means.

5. The check valve according to claim 1, wherein said preselected distance determines a forward cracking pressure of the check valve and said forward cracking pressure comprises the range of from about 0 psi to about 1.5 psi.

6. The check valve according to claim 5, wherein said forward cracking pressure comprises a function of the thickness of said piece and said predetermined width of each said web.

7. The check valve according to claim 6, wherein said forward cracking pressure is optimized for a combined surface area of said windows.

8. The check valve according to claim 7, wherein said combined surfaced area of said windows is decreased with increases in said preselected distance.

9. A system for administration of solutions, comprising:
   a fluid source containing one solution;
   means for delivering said one solution to a patient; and
   an antireflux valve for said means for delivering said one solution, said antireflux valve comprising:
      a valve disk;
      first housing means housing said valve disk, said first housing means including an inlet, a valve seat, and a first valve disk retaining surface;
      second housing means including an outlet, and a second valve disk retaining surface;
      said first and second housing means adapted to be snap-fit together such that said valve disk is retained between said first and second valve disk retaining surfaces; and
      said valve disk comprises:
      a flat, circular piece of flexible material with a Shore A durometer hardness in the range of about 35-100 having at least three arcuately-shaped windows formed in said piece, each adjacent window being separated by a web of predetermined width;
      a sealing annulus at the outer periphery of said piece, said sealing annulus being defined by the formation of said windows; and
      a central closure for closing the valve seat of the check valve, said closure being defined by the formation of said windows concentrically inward from said windows and attached to said sealing annulus by said webs.

10. The system according to claim 9, wherein said means for delivering said one solution is selected from the group consisting of gravity flow, a pressure cuff, a syringe pump and a peristaltic pump.

11. The system according to claim 9, wherein said antireflux valve has a preselected minimum hysteresis in a direction from said second housing means toward said first housing means.

12. The system according to claim 11, wherein said antireflux valve has a negative resistance to flow in a direction from said first housing means toward said second housing means.

13. The system according to claim 12, wherein said antireflux valve is adapted to close at a pressure of more than about 200 mm Hg.

14. The system according to claim 9, further comprising:
   a fluid source containing another solution;
   means for delivering said other solution to a patient; and
   a check valve for said means for delivering said other solution, said check valve comprising:

another valve disk;

third housing means housing said other valve disk, said third housing means including an inlet, a valve seat, and a third valve disk retaining surface;

fourth housing means including an outlet, and a fourth valve disk retaining surface;

said third and fourth housing means adapted to be snap-fit together such that said other valve disk is retained between said third and fourth valve disk retaining surfaces; and said other valve disk comprises:

a flat, circular piece of flexible material with a Shore A durometer hardness in the range of about 35-100 having at least three arcuately-shaped windows formed in said piece, each adjacent window being separated by a web of predetermined width;

a sealing annulus at the outer periphery of said piece, said sealing annulus being defined by the formation of said windows; and a central closure for closing the valve seat of the check valve, said closure being defined by the formation of said windows concentrically inward from said windows and attached to said sealing annulus by said webs.

15. The system according to claim 14, further comprising a fitting for joining said means for delivering said one solution and said other solution, whereby both solutions are adapted to be delivered to the patient.

16. The system according to claim 15, wherein said valve seat of said check valve is adapted to extend below a level of said third valve disk retaining surface, in the direction of said fourth valve disk retaining surface, thereby providing preselected amounts of preloading of said closing means of said check valve.

17. The system according to claim 16, wherein said valve seat is extended to provide said preload in the range of from about 0-400 mm Hg.

* * * * *